United States Patent [19]

Schmid et al.

[11] Patent Number: 4,685,969

[45] Date of Patent: Aug. 11, 1987

[54] PROCESS AND SEPARATING SUBSTANCE FOR REMOVING A CAVITY-POLYMERIZED INLAY CONSISTING OF A DENTAL FILLING COMPOSITE

[75] Inventors: Adalbert Schmid, Rebstein; Alfons Kiener, Heerbrugg; Stephan Kägi, Widnau; Jean P. Claude, Altstätten, all of Switzerland

[73] Assignee: Coltene AG, Altstatten

[21] Appl. No.: 801,763

[22] Filed: Nov. 26, 1985

[30] Foreign Application Priority Data

Dec. 5, 1984 [CH] Switzerland ............... 5779/84

[51] Int. Cl.$^4$ .................................................. A61K 6/08
[52] U.S. Cl. .................................... 106/35; 433/228.1
[58] Field of Search .................... 433/201.1, 228.1; 106/35

[56] References Cited

U.S. PATENT DOCUMENTS

Re. 21,779 4/1941 Schlesinger ............... 433/228.1
4,362,510 12/1982 Brauer et al. ............ 433/228.1 X
4,431,451 2/1984 Mabie et al. ............. 433/201.1 X

FOREIGN PATENT DOCUMENTS 50-49358 5/1975 Japan ............... 433/228.1

Primary Examiner—Nancy A. Swisher
Attorney, Agent, or Firm—Murray and Whisenhunt

[57] ABSTRACT

Process for separating a pre-polymerized composite dental filling, such as an inlay, from the hard substance of the tooth using a separating substance consisting of a sol formed from a substance swollen and dissolved in alcohol and forming an organic or inorganic gel. The separating substance is applied as a separating layer to the cavity prior to introducing the composite into the cavity and this facilitates the removal of the composite after hardening in the cavity. The separating layer is removed from the cavity, and the inlay is then cemented into the cavity after being tempered.

12 Claims, No Drawings

PROCESS AND SEPARATING SUBSTANCE FOR REMOVING A CAVITY-POLYMERIZED INLAY CONSISTING OF A DENTAL FILLING COMPOSITE

The invention concerns a process and a separating substance for removing an inlay, polymerized in a cavity and made of a composite dental filling, principally for placing directly a composite dental filling, especially an inlay, in the region of the molars and pre-molars.

BACKGROUND OF THE INVENTION

Today, composite dental fillings are used increasingly and have completely displaced the use of amalgams in the area of the front teeth, mostly for aesthetic reasons. As regards the region of the lateral teeth, however, composite dental fillings have not gained wide acceptance because of the absence of certain properties which are required for clinical uccess.

Among the properties required for composite dental fillings are freedom from pores, X-ray opacity, resistance to abrasion and complete edge seal. There have been many attempts to achieve these properties in order to make available the undisputed aesthetic advantages associated with composite dental fillings as well as the possibility of mercury-free fillings for the dental side regions.

The problem relating to freedom from pores has been solved quite satisfactorily by the introduction of light-hardening composites, whereby manual mixing is no longer required. X-ray opacity is achievable by the use of special glass fillers doped with heavy metals such as barium or strontium. To improve resistance to abrasion and thereby minimize material wear of the filling substance, various improvements have been suggested which do not give excellent results, but which have, nevertheless, proved adequate. For example, the tearing-loose of filler particles from the resin matrix giving rise to rough surfaces, and hence rapid abrasion, has been reduced by treating the filler particles with special bonding agents (for instance silane). This procedure allows the formation of a chemicl bond between the resin matrix and the filler to resist large stresses. Additionally the particle size of the filler has been optimized. Thus, these new and so-called "hybrid composites" contain fillers with an average particle size in the range of about 0.5 and 5 microns($\mu$) and a proportion of highly dispersed silicic acid. Such particles can neither project much above the filling surface nor, if tearing loose, leave a large crater behind that would weaken the entire filling. Nevertheless they exhibit a high Young's modulus and adequate hardness.

Despite the above improvements, the problem of obtaining a complete edge seal still exists. This intactness is required so that microorganisms are prevented from entering the edge gap between the filling and the tooth and possibly causing the formation of secondary caries. The edge gap is caused by the polymerization shrinkage. All known composites have shrinkage values of about 2.5% by volume and larger. Prevention of the formation of an edge gap has already been attempted by bonding the filling to the hard substance of the tooth using an adhesive. So far this has been successful only for relatively small fillings, with shrinkages of a few microns which are wholly within the enamel area. However, for larger fillings, such an adhesive technique is not entirely satisfactory since the bonding means for dentine cannot resist the shrinkage forces of larger fillings, and for normal oral techniques, the restored work becomes rapidly leaky. While improvements have been achieved using various applicat.ion techniques such as build-up in layers and shrinkage vector reversal (hardening from the side of the tooth), they have nevertheless proved inadequate for clinical success.

A new preparation for improving the sealing of the edge consists in a composite inlay which is similar to the long known gold and ceramic inlays of dentistry. First the dentist takes an impression of the cavity to be filled using an elastomeric impression material. The cavity is then temporarily closed and the patient is discharged. The dental technician then makes a hard plaster model of this impression mold. The hard plaster model is divided into model segments, and thereupon the modeling with composite takes place. A light-hardening substance is used, which is polymerized by direct illumination on the stump model. To achieve better physical properties, especially good abrasion resistance and Young's modulus, the stump model after removal of the inlay is improved in an oven for instance 15 minutes at 100° C. or 5 to 10 minutes at 120° C. The removed inlay is finished and polished can be inserted into the patient after the dentist has taken out the stop-gap filling and cleaned and dried the cavity.

In the first instance, the above known procedure allows the use of an optimally shaped and hardened material which is polymerized completely before being inserted and so will not shrink any further. Accordingly an optimal edge seal is also obtained in conjunction with the cement used to bond the inlay to the tooth. Further it is possible to achieve good contact points, ideal occlusion-shaping and the prevention of excess, especially at the near cervical edge. However this procedure is very complex and time-consuming. The patient must call at least twice on the dentist and a stop-gap filling is mandatory. Additionally, there is the danger of mistakes occurring during the long finishing stage, whereby the work would have to be repeated. Furthermore, the procedure cannot be shortened because it has been impossible so far to post-process a pre-polymerized inlay because this inlay cannot be removed from the cavity without destroying its shape.

OBJECTS OF THE INVENTION

It is therefore a primary object of the present invention to provide an improved process for the direct emplacement of a composite inlay in a tooth, thereby eliminating the need for any modeling by a dental technician.

It is another object of the present invention to provide a separating substance for facilitating the removal of a composite dental filling such as an inlay from a cavity.

DESCRIPTION OF THE INVENTION

According to one aspect, the invention provides a process for introducing a dental filling into a tooth cavity comprising the steps of preparing the tooth cavity, introducing a separating solution into the cavity to form an insulating layer on the cavity, the separating solution decomposing into a sol at body temperature, applying a composite to the separating layer, tamping the composite into the cavity and against the separating layer, partly hardening the composite in one or more steps to form a partly hardened filling, roughly fitting the partly harened filling in the cavity, removing the partly hardened filling from the cavity, hardening the filling to completion together with any further mechanical processing ich may be required to form a completely hardened filling, removing the separating layer from a cavity, and bonding the completely hardened filling in the cavity.

According to another aspect of the invention, there is provided a separating substance for use in the process of the invention, consisting of a solution which decomposes into a sol at body temperature.

Preferably, the sol comprises a gel-forming component and an alcohol. Upon evaporation of the alcohol, the separating substance forms a thin film of gel, which prevents the composite from bonding to the dentine, and thereby makes possible removal of the filling.

By using the separating substance of the invention, it is now possible, surprisingly, to remove from a cavity a composite polymerized in the caity without destroying the precise shape and surface of the composite, and to externally polymerize to completion and post-process the composite. The solution for the separating layer is used in the gelled state for ease of application. Upon being heated to body temperature, the layer decomposes into a sol and thereby produces a separating effect.

Less than 45 minutes are required by the process of invention from the readying of the cavity to polishing the filled tooth. The process offers the great advantage that the dentist can now emplace an inlay in a single treatment, in contrast to the known procedures which require several days.

Implementation of the process depends on a proper inlay preparation and especially on the separating solution which for the first time makes it possible to remove the inlay polymerized in the cavity for purposes of further processing without damaging the inlay.

In a further embodiment of the invention, a matrix bond is fastened to the cavity to mold the tooth. This matrix bond also can be made to curve if necessary.

Advantageously, the composite is a hybrid composite which is hardenable under the action of light. The composite is used with transparent wedges fixing matrix bond in place to facilitate the partial hardening.

The sol is preferably obtained from a gelling component and a hydrophilic solution. Alcohols are preferred, hydrophilic solutions, and ethyl alcohol is best suited because it is physiologically unobjectionable.

However, other hydrophilic organic solutions can be used to prepare the separating solution, such as short-chain alcohols, eg. methanol or isopropanol, ketones, eg. acetone, methylethylketone, or aldehydes, eg. ethanal and propanal.

The gelling component may be an organic or inorganic swelling means. Advantageously the gelling component is an organic swelling means.

Appropriately the gelling component first is made to swell by a hydrophilic solution and then is converted into the sol.

Suitable organic swelling means are methylcellulose, polysaccharides, pectins, agar and gelatins. Agar has been found to be especially advantageous; it is used in a proportion of 0.5 to 5% by weight, preferably about 3% by weight, in alcohol-water, the ratio of alcohol to water being about 1:1.

Suitable inorganic swelling means are aluminum hydroxides, silicic acid and montmorillonite. Aluminum hydroxide gel free of alkali has been found to be especially advantageous.

Preferably the composite tooth filling material consists of a hybrid composite of 15 to 30% by weight of a resin matrix with end-located methacrylic groups and 70 to 85% by weight of an X-ray opaque glass filler with an average particle size of 0.5 to 5$\mu$, where from 0 to 10% by weight of the glass filler can be replaced by highly dispersed silicic acid. Such a composite tooth filling exhibits especially high resistance to abrasion and can be relatively easily removed from the cavity when the separating solution is used. Other compositions of dental filling composites are also conceivable.

The use of the separating substance of the invention is especially suited for the direct emplacement of inlays in the region of the premolars and molars.

For purposes of illustration, the procedure employed to install an inlay with the separating substance of the invention is described below.

After the tooth cavity has been readied and the rectangularly prepared edges have been smoothed in known manner, a matrix bond to shape the tooth is wedged in place and if necessary made curved. Advantageously transparent wedges (HAWE-NEOS DENTAL) can be used, which allow light polymerization from the cervix. A cavity liner is placed to cover the dentine of the tooth. Glass ionomer cement may be used to place the dentine covering layer. Thereupon, the separating substance in the form of a solution is introdced by spraying or with a brush to produce a separating layer in the cavity.

A first portion of a suitable composite is applied in known mesial-occlusal manner on the separating layer and tamped into place with a spherical tamper. A second portion is placed into distal-occlusal part and tamped into place. Another portion is placed on to the occlusal and roughly shaped with the spherical tamper for its anatomical form. The completely filled cavity is then illuminated for one minute through each transparent wedge and one minute from the occlusal with a light having a wavelength from 450 to 500 nm and a power of about 222 mw per $cm^2$.

The matrix bond is removed but the wedges however remain in position. Rough removal of the occlusal-palatinal-lingualbuccal excesses is then undertaken. A metal spatula is used to remove the inlay. Any problem points are removed using a rotating instrument. The pre-polymerized inlay is put back on the tooth and removed after the check. To harden completely, the inlay is upgraded for about 15 minutes at 100° C. or about 5 to 10 minutes at about 120° C. in an oven, possibly with additional light activation. After the separating substance has been removed from the cavity, for instance by intensive rinsing with water, the dental enamel edges are etched. Prior to cementing, the inlay inner surfaces are slightly roughened by a diamond, and the dental enamel is reacted in known manner with a chemically hardening resin solution consisting of a mixture of Bowen resins with additive stabilizers, initiators and activators, possibly with special bonding reinforcing means for dental enamel andr dentine. Then they are coated and the inlay is cemented in place by a fluid composite, preferably a hybrid composite, in known manner.

The cementing composites preferably consist of 2-component light curing material provided for optimal edge matching with a very fine particulate filler of which the average particle size is between 0.2 and 3$\mu$ and of whch the filling degree is about 50 to 75% by weight. The cementing composite, after the inlay is pressed into its final position, then is illuminated by a light for one minute through each wedge and one minute from the occlusal. An opaque and X-ray opaque composition is recommended for visual and X-ray checks. It is important that a high-grade composite be used for the cementing operation to prevent erosion of the cement gap. After removing occlusal excesses, for instance using paper discs or strips, the inlay can be finished and polished. The whole procedure lasts approximately 30 to 45 minutes.

The invention will now be further illustrated by the following Examples.

EXAMPLE 1

| | |
|---|---|
| Agar | 3.00 g |
| water | 47.00 |
| 96% ethanol | 50.00 |
| | 100.00 g |

The pulverulent agar is first made to swell in water for 10 minutes. The swollen agar is then reacted with the ethanol and dispersed with strong agitation into a colloidal sol.

EXAMPLE 2

10 g of cellulose ether of the types (one experiment per type) MW 6,000, MK 20,000, CRW 5,000 from Wolff, Walsode AG, Germany, were boiled for 10 minutes in 500 ml of 50% by volume alcohol water. Following cooling a gel is formed which offers an excellent separating effect.

EXAMPLE 3

80 g of a hydrophilic, highly dispersed silicic acid (HDK V 15 from Wacker Chemie, Munich) were reacted with 920 ml of a 50% by volume water alcohol and boiled with reflux for 10 minutes. A gel with good separating properties is obtained.

EXAMPLE 4

50 g of gelatin and 950 ml of 1:1 water-alcohol are heated to boiling for 10 minutes. A gel with good separating properties is obtained after cooling.

EXAMPLE 5

10 g of gelatin, 5 g of agar and 990 ml of a 50% by water-alcohol mixture are heated together at reflux and are left to boil for 10 minutes. A stable gel with excellent separating properties is obtained.

EXAMPLE 6

In this example, the process of the invention will be illustrated utilizing the separating substance of Example 1. About 0.2 g of the colloidal sol separating substance of Example 1 was applied to a tooth having a ready-prepared cavity. The whole tooth was covered by the separating substance in order to help remove the inlay because of possible occlusal excesses. Several portions of a hybrid dental filling composite having the following composition were used to fill the cavity.

Resin: Bisphenol A diglycidylmethacrylate diluted with a difunctional reactive monomer;
Filler: barium aluminum silicate glass containing less than 10% silica, with an average particle size of 1-2 microns;
Filler Load; approximately 78%

The filling was partly hardened, when all of the composite had been introduced into the cavity, using a lamp having a power of 222 mv/cm$^2$, under the following conditions:

1 minute through each of the wedges;
1 minute from occlusal

The partly hardened filling was then removed from the cavity and completely hardened at a temperature of about 100° C. and using a 50 watt halogen bulb for a period of about 7 minutes. The separating layer was removed from the cavity by rinsing with water, and the completely hardened filling was then cemented in the cavity using, as adhesive, the same composition as the composite material with a reduced amount of filler.

The separating substance of the invention, preferably obtained according to Examples 1 and 2, has made it possible, contrary to the assumptions of the expert profession, to directly put an inlay in place. As a consequence, many work steps can be circumvented, and a saving in expensive material may also be realized.

We claim:

1. A process for filling a tooth cavity with a composite dental filling, said process comprising the steps of:
   preparing the tooth cavity;
   introducing a separating substance into said cavity to form a separating layer in said cavity, said separating substance decomposing at body temperature into a sol;
   introducing a dental filling composite into said cavity;
   partly hardening said composite in said cavity and roughly fitting said composite in said cavity to form a partly hardened filling;
   removing said partly hardened filling from said cavity;
   completing the hardening of the partly hardened filling to form a completely hardened filling;
   removing said separating layer from said cavity; and
   bonding said completely hardened filling in said cavity.

2. A process according to claim 1, wherein a female mold is fastened to the cavity to shape the tooth.

3. A process according to claim 1, wherein said composite is a light-hardening hybrid composite.

4. A separating substance for use in the process as claimed in claim 1, said separating substance comprising a solution which decomposes into a sol at body temperature.

5. A separating substance according to claim 4, wherein the sol consists of a gel-forming component and a hydrophilic solution.

6. A separating substance according to claim 5, wherein said hydrophilic solution is an alcohol.

7. A separating substance according to claim 6, wherein said alcohol is ethyl alcohol.

8. A separating substance according to claim 5, wherein said gel-forming component is an organic swelling means.

9. A separating substance according to claim 8, wherein the organic swelling means is agar.

10. A separating substance according to claim 9, wherein the agar is present in a 1:1 alcohol water mixture in an amount of about 0.5 to 5% by weight.

11. A separating substance according to claim 5, wherein the gel-forming component is an inorganic swelling means.

12. A separating substance according to claim 11, wherein the inorganic swelling means is aluminum hydroxide.

* * * * *

UNITED STATES PATENT AND TRADEMARK OFFICE
CERTIFICATE OF CORRECTION

PATENT NO. : 4,685,969
DATED : August 11, 1987
INVENTOR(S) : SCHMID et al

It is certified that error appears in the above-identified patent and that said Letters Patent is hereby corrected as shown below:

Front page of the patent, right hand column under "U.S. Patent Documents" delete "Mabie" and replace by --Marbie--

Col. 1 line 43 replace "chemicl" by --chemical--
Col. 2 line 4 replace "applicat.ion" by --application--
Col. 2 line 67 replace "harened" by --hardened--
Col. 3 line 2 replace "ich" by --which--
Col. 3 line 17 replace "caity" by --cavity--
Col. 3 line 37 replace "bond" by --band--
Col. 3 line 38 replace "bond" by --band--
Col. 3 line 42 replace "bond" by --band--
Col. 4 line 20 replace "bond" by --band--
Col. 4 line 41 replace "bond" by --band--
Col. 4 line 59 replace "andr" by --and/or--
Col. 5 line 29 replace "Walsode" by --Walsrode--
Col. 6 line 1 replace "mv/cm$^2$" by --mw/cm$^2$--
Col. 6 line 39/40 replace "female mold" by --matrix band--

Signed and Sealed this

Thirty-first Day of May, 1988

Attest:

DONALD J. QUIGG

Attesting Officer

Commissioner of Patents and Trademarks